United States Patent
Seo et al.

(10) Patent No.: US 9,551,038 B2
(45) Date of Patent: Jan. 24, 2017

(54) SYSTEM FOR INTEGRATED ANALYSIS OF REAL-TIME POLYMERASE CHAIN REACTION AND DNA CHIP AND METHOD FOR INTEGRATED ANALYSIS USING THE SAME

(75) Inventors: Sung-Min Seo, Seoul (KR); Do-Bu Lee, Incheon (KR); Joong Hwan Lee, Daejeon (KR); Mun-Cheol Paek, Daejeon (KR); Su-Jin Ku, Daejeon (KR)

(73) Assignee: K-MAC, Daejeon (KR)

( * ) Notice: Subject to any disclaimer, the term of this patent is extended or adjusted under 35 U.S.C. 154(b) by 0 days.

(21) Appl. No.: 13/554,348

(22) Filed: Jul. 20, 2012

(65) Prior Publication Data

US 2013/0303390 A1    Nov. 14, 2013

(30) Foreign Application Priority Data

May 11, 2012    (KR) .......................... 10-2012-0050500

(51) Int. Cl.
*C12Q 1/68* (2006.01)
*C12P 19/34* (2006.01)
(Continued)

(52) U.S. Cl.
CPC ......... *C12Q 1/6888* (2013.01); *B01L 3/50825* (2013.01); *B01L 3/50851* (2013.01);
(Continued)

(58) Field of Classification Search
CPC ....... C12Q 1/686; C12Q 1/6888; C12Q 1/689; C12Q 1/706; C12Q 2561/113; C12Q 2565/501; B01L 2300/046; B01L 2300/0636; B01L 2300/0663; B01L 2300/0829; B01L 2300/0851; B01L 3/50825; B01L 3/50851; B01L 3/50853; B01L 7/52
See application file for complete search history.

(56) References Cited

U.S. PATENT DOCUMENTS 6,632,641 B1 * 10/2003 Brennan ................ C12Q 1/686
                                                                    435/287.2
6,670,130 B1 * 12/2003 Kim ...................... C07K 14/35
                                                                    435/6.16
(Continued)

FOREIGN PATENT DOCUMENTS

CN           1869247 A       11/2006
DE    WO 2007131995 A1 *  11/2007 .......... B01J 19/0046
(Continued)

OTHER PUBLICATIONS

Legally and Soh, "Integrated Genetic Analysis Microsystems", Critical Reviews in Solid State and Materials Sciences, vol. 39, p. 207-233 (2005).*

(Continued)

*Primary Examiner* — Young J Kim
(74) *Attorney, Agent, or Firm* — Hauptman Ham, LLP

(57) ABSTRACT

Provided are a system for integrated analysis of a real-time polymerase chain reaction and a DNA chip and a method for integrated analysis using the same, and more particularly to an apparatus for integrated analysis of a real-time polymerase chain reaction and a DNA chip and a method for integrated analysis using the same. According to the method for integrated analysis of a biomaterial of the present invention, gene amplification proceeds and subsequently hybridization proceeds in a single reactor, thereby preventing contamination of the sample due to external factors, which may be caused while the sample is transferred for reaction, and automating a series of procedures such as injection of the sample, reaction of the biomaterial, and detection and analysis of results.

4 Claims, 6 Drawing Sheets

(51) Int. Cl.
  *B01L 3/00* (2006.01)
  *C12Q 1/70* (2006.01)
  *B01L 7/00* (2006.01)

(52) U.S. Cl.
  CPC ............ *B01L 3/50853* (2013.01); *B01L 7/52* (2013.01); *C12Q 1/686* (2013.01); *C12Q 1/689* (2013.01); *C12Q 1/706* (2013.01); *B01L 2300/046* (2013.01); *B01L 2300/0636* (2013.01); *B01L 2300/0663* (2013.01); *B01L 2300/0829* (2013.01); *B01L 2300/0851* (2013.01)

(56) References Cited

U.S. PATENT DOCUMENTS

| | | | |
|---|---|---|---|
| 6,770,441 | B2 | 8/2004 | Dickinson et al. |
| 7,332,328 | B2 | 2/2008 | Webb et al. |
| 7,807,448 | B2 * | 10/2010 | Glezer ............... B01L 3/5025 422/425 |
| 2002/0146735 | A1 | 10/2002 | Franzen |
| 2003/0124029 | A1 * | 7/2003 | Webb ............... G01N 35/028 435/287.2 |
| 2004/0110269 | A1 * | 6/2004 | Vipond et al. ............. 435/252.3 |
| 2006/0234236 | A1 | 10/2006 | Gumbrecht et al. |

FOREIGN PATENT DOCUMENTS

| | | |
|---|---|---|
| JP | 2000511060 A | 8/2000 |
| JP | 2002122596 A | 4/2002 |
| JP | 2002176985 A | 6/2002 |
| JP | 2004535162 A | 11/2004 |
| JP | 2009537126 A | 10/2009 |
| JP | 2010-032487 A | 2/2010 |
| WO | 9745559 A1 | 12/1997 |
| WO | 2004024949 A2 | 3/2004 |
| WO | 2007131995 A1 | 11/2007 |
| WO | 2008034896 A2 | 3/2008 |
| WO | 2010119396 A1 | 10/2010 |
| WO | 2012108499 A1 | 8/2012 |

OTHER PUBLICATIONS

Shen et al., "Multiplexed Quantification of Nucleic Acids with Large Dynamic Range Using Multivolume Digital RT-PCR on a Rotational SlipChip Tested with HIV and Hepatitis C Viral Load", Journal of the American Chemical Society, vol. 133, p. 17705-17712 (2011).*
SnagIt capture of Score for SEQ ID No. 4 matching Vinold SEQ ID No. 102 (and others), p. 1, (2013).*
Teo et al., "VereFluTM: an integrated multiplex RT-PCR and microarray assay for rapid detection and identification of human influenza A and B viruses using lab-on-chip technology", Archives of Virology, vol. 156, p. 1371-1378 (published online Apr. 19, 2011).*
VereFluTM brochure, p. 1-2 (accessed on Apr. 30, 2013 from http://www.vereduslabs.com/images/stories/pdf/VereFluBrochure.pdf).*
Lagally and Soh, "Integrated Genetic Analysis Microsystems", Critical Reviews in Solid State and Materials Sciences, vol. 39, p. 207-233 (2005).*
Canadian Office Action dated Nov. 4, 2014.
Japanese Notice of Allowance dated Jan. 6, 2015.
Australian Office Action dated Sep. 12, 2013.
Kolchinsky A. et al., Analysis of SNPs and Other Genomic Variations Using Gel-Based Chips, Review Article, Feb. 4, 2002, vol. 19, p. 343-360, Wiley-Liss, Inc.
Japanese Office Action dated Feb. 4, 2014.

* cited by examiner

A

B

A

B

MTB/NTM Genotyping (RT-PCR)

MTB MDR Detection (DNA chip)

SEQUENCE LISTING

<160> NUMBER OF SEQ ID NOS: 46

<210> SEQ ID NO 1
<211> LENGTH: 20
<212> TYPE: DNA
<213> ORGANISM: Mycobacterium tuberculosis

<400> SEQUENCE: 1
gctttctaag gagcaccacg                                            20

<210> SEQ ID NO 2
<211> LENGTH: 20
<212> TYPE: DNA
<213> ORGANISM: Mycobacterium tuberculosis

<400> SEQUENCE: 2
tggatagtgg ttgcgagcat                                            20

<210> SEQ ID NO 3
<211> LENGTH: 20
<212> TYPE: DNA
<213> ORGANISM: Mycobacterium tuberculosis

<400> SEQUENCE: 3
tggtggggcg taggccgtga                                            20

<210> SEQ ID NO 4
<211> LENGTH: 20
<212> TYPE: DNA
<213> ORGANISM: Mycobacterium tuberculosis

```
<400> SEQUENCE: 4
gctggtcatg ttcgcgatcg                                          20

<210> SEQ ID NO 5
<211> LENGTH: 19
<212> TYPE: DNA
<213> ORGANISM: Mycobacterium tuberculosis

<400> SEQUENCE: 5
accggttacc gccagcgag                                           19

<210> SEQ ID NO 6
<211> LENGTH: 20
<212> TYPE: DNA
<213> ORGANISM: Mycobacterium tuberculosis

<400> SEQUENCE: 6
accccagtgc gaaagttccc                                          20

<210> SEQ ID NO 7
<211> LENGTH: 20
<212> TYPE: DNA
<213> ORGANISM: Mycobacterium tuberculosis

<400> SEQUENCE: 7
ggtaaccagg actgaacggg                                          20

<210> SEQ ID NO 8
<211> LENGTH: 20
<212> TYPE: DNA
<213> ORGANISM: Mycobacterium tuberculosis

<400> SEQUENCE: 8
aagagctcgt atggcaccgg                                          20

<210> SEQ ID NO 9
<211> LENGTH: 19
<212> TYPE: DNA
<213> ORGANISM: Mycobacterium tuberculosis

<400> SEQUENCE: 9
agcgccagca gggctcttc                                           19

<210> SEQ ID NO 10
<211> LENGTH: 20
<212> TYPE: DNA
<213> ORGANISM: Mycobacterium tuberculosis

<400> SEQUENCE: 10
cagccagctg agccaattca                                          20

<210> SEQ ID NO 11
<211> LENGTH: 15
<212> TYPE: DNA
<213> ORGANISM: Mycobacterium tuberculosis

<400> SEQUENCE: 11
agccagccga gccaa                                               15

<210> SEQ ID NO 12
<211> LENGTH: 15
<212> TYPE: DNA
```

```
<213> ORGANISM: Mycobacterium tuberculosis

<400> SEQUENCE: 12
ctgagccaat tcatg                                                    15

<210> SEQ ID NO 13
<211> LENGTH: 16
<212> TYPE: DNA
<213> ORGANISM: Mycobacterium tuberculosis

<400> SEQUENCE: 13
ctgagcctat tcatgg                                                   16

<210> SEQ ID NO 14
<211> LENGTH: 16
<212> TYPE: DNA
<213> ORGANISM: Mycobacterium tuberculosis

<400> SEQUENCE: 14
ttcatggacc agaaca                                                   16

<210> SEQ ID NO 15
<211> LENGTH: 16
<212> TYPE: DNA
<213> ORGANISM: Mycobacterium tuberculosis

<400> SEQUENCE: 15
ttcatggtcc agaaca                                                   16

<210> SEQ ID NO 16
<211> LENGTH: 17
<212> TYPE: DNA
<213> ORGANISM: Mycobacterium tuberculosis

<400> SEQUENCE: 16
attcatgtac cagaaca                                                  17

<210> SEQ ID NO 17
<211> LENGTH: 17
<212> TYPE: DNA
<213> ORGANISM: Mycobacterium tuberculosis

<400> SEQUENCE: 17
attcatgttc cagaaca                                                  17

<210> SEQ ID NO 18
<211> LENGTH: 14
<212> TYPE: DNA
<213> ORGANISM: Mycobacterium tuberculosis

<400> SEQUENCE: 18
ctgtcggggt tgac                                                     14

<210> SEQ ID NO 19
<211> LENGTH: 14
<212> TYPE: DNA
<213> ORGANISM: Mycobacterium tuberculosis

<400> SEQUENCE: 19
ctgttggggt tgac                                                     14

<210> SEQ ID NO 20
<211> LENGTH: 19
```

```
<212> TYPE: DNA
<213> ORGANISM: Mycobacterium tuberculosis

<400> SEQUENCE: 20
gttgacccac aagcgccga                                          19

<210> SEQ ID NO 21
<211> LENGTH: 17
<212> TYPE: DNA
<213> ORGANISM: Mycobacterium tuberculosis

<400> SEQUENCE: 21
ggttgaccta caagcgc                                            17

<210> SEQ ID NO 22
<211> LENGTH: 17
<212> TYPE: DNA
<213> ORGANISM: Mycobacterium tuberculosis

<400> SEQUENCE: 22
ggttgaccga caagcgc                                            17

<210> SEQ ID NO 23
<211> LENGTH: 15
<212> TYPE: DNA
<213> ORGANISM: Mycobacterium tuberculosis

<400> SEQUENCE: 23
ttgacccgca agcgc                                              15

<210> SEQ ID NO 24
<211> LENGTH: 15
<212> TYPE: DNA
<213> ORGANISM: Mycobacterium tuberculosis

<400> SEQUENCE: 24
ttgaccctca agcgc                                              15

<210> SEQ ID NO 25
<211> LENGTH: 15
<212> TYPE: DNA
<213> ORGANISM: Mycobacterium tuberculosis

<400> SEQUENCE: 25
ttgaccccca agcgc                                              15

<210> SEQ ID NO 26
<211> LENGTH: 15
<212> TYPE: DNA
<213> ORGANISM: Mycobacterium tuberculosis

<400> SEQUENCE: 26
cgactgtcgg cgctg                                              15

<210> SEQ ID NO 27
<211> LENGTH: 15
<212> TYPE: DNA
<213> ORGANISM: Mycobacterium tuberculosis

<400> SEQUENCE: 27
cgactgttgg cgctg                                              15

<210> SEQ ID NO 28
```

-continued

<210> SEQ ID NO 28
<211> LENGTH: 15
<212> TYPE: DNA
<213> ORGANISM: Mycobacterium tuberculosis

<400> SEQUENCE: 28
ccgactgtga gcgct                                                      15

<210> SEQ ID NO 29
<211> LENGTH: 16
<212> TYPE: DNA
<213> ORGANISM: Mycobacterium tuberculosis

<400> SEQUENCE: 29
ggcgctgggg cccggc                                                     16

<210> SEQ ID NO 30
<211> LENGTH: 17
<212> TYPE: DNA
<213> ORGANISM: Mycobacterium tuberculosis

<400> SEQUENCE: 30
gtcggcgccg gggcccg                                                    17

<210> SEQ ID NO 31
<211> LENGTH: 15
<212> TYPE: DNA
<213> ORGANISM: Mycobacterium tuberculosis

<400> SEQUENCE: 31
atcaccagcg gcatc                                                      15

<210> SEQ ID NO 32
<211> LENGTH: 15
<212> TYPE: DNA
<213> ORGANISM: Mycobacterium tuberculosis

<400> SEQUENCE: 32
atcaccaccg gcatc                                                      15

<210> SEQ ID NO 33
<211> LENGTH: 15
<212> TYPE: DNA
<213> ORGANISM: Mycobacterium tuberculosis

<400> SEQUENCE: 33
atcaccaacg gcatc                                                      15

<210> SEQ ID NO 34
<211> LENGTH: 15
<212> TYPE: DNA
<213> ORGANISM: Mycobacterium tuberculosis

<400> SEQUENCE: 34
ggcgagacga taggt                                                      15

<210> SEQ ID NO 35
<211> LENGTH: 15
<212> TYPE: DNA
<213> ORGANISM: Mycobacterium tuberculosis

<400> SEQUENCE: 35
ggcgagatga taggt                                                      15

-continued

```
<210> SEQ ID NO 36
<211> LENGTH: 20
<212> TYPE: DNA
<213> ORGANISM: Hepatitis B virus

<400> SEQUENCE: 36
tcctgctgct atgcctcatc                                              20

<210> SEQ ID NO 37
<211> LENGTH: 31
<212> TYPE: DNA
<213> ORGANISM: Hepatitis B Virus

<400> SEQUENCE: 37
tcccttaact tcatgggata tgtcgacgga a                                 31

<210> SEQ ID NO 38
<211> LENGTH: 19
<212> TYPE: DNA
<213> ORGANISM: Hepatitis B Virus

<400> SEQUENCE: 38
tggtattggg gccaagtct                                               19

<210> SEQ ID NO 39
<211> LENGTH: 15
<212> TYPE: DNA
<213> ORGANISM: Hepatitis B Virus

<400> SEQUENCE: 39
tgggctttcg caaaa                                                   15

<210> SEQ ID NO 40
<211> LENGTH: 15
<212> TYPE: DNA
<213> ORGANISM: Hepatitis B Virus

<400> SEQUENCE: 40
tgggcttccg caaaa                                                   15

<210> SEQ ID NO 41
<211> LENGTH: 15
<212> TYPE: DNA
<213> ORGANISM: Hepatitis B Virus

<400> SEQUENCE: 41
tgggcttacg caaaa                                                   15

<210> SEQ ID NO 42
<211> LENGTH: 15
<212> TYPE: DNA
<213> ORGANISM: Hepatitis B Virus

<400> SEQUENCE: 42
tgggcttgcg caaaa                                                   15

<210> SEQ ID NO 43
<211> LENGTH: 15
<212> TYPE: DNA
<213> ORGANISM: Hepatitis B Virus

<400> SEQUENCE: 43
tgggccttcg caaaa                                                   15
```

```
<210> SEQ ID NO 44
<211> LENGTH: 15
<212> TYPE: DNA
<213> ORGANISM: Hepatitis B Virus

<400> SEQUENCE: 44
tgggcctccg caaaa                                               15

<210> SEQ ID NO 45
<211> LENGTH: 15
<212> TYPE: DNA
<213> ORGANISM: Hepatitis B Virus

<400> SEQUENCE: 45
tgggcctacg caaaa                                               15

<210> SEQ ID NO 46
<211> LENGTH: 15
<212> TYPE: DNA
<213> ORGANISM: Hepatitis B Virus

<400> SEQUENCE: 46
tgggcctagg caaaa                                               15
```

SYSTEM FOR INTEGRATED ANALYSIS OF REAL-TIME POLYMERASE CHAIN REACTION AND DNA CHIP AND METHOD FOR INTEGRATED ANALYSIS USING THE SAME

CROSS-REFERENCE TO RELATED APPLICATIONS

This application claims priority under 35 U.S.C. §119 to Korean Patent Application No. 10-2012-0050500, filed on 11 May, 2012, in the Korean Intellectual Property Office, the disclosure of which is incorporated herein by reference in its entirety.

TECHNICAL FIELD

The following disclosure relates to a system for integrated analysis of a real-time polymerase chain reaction and a DNA chip and a method for integrated analysis using the same, and more particularly to an apparatus for integrated analysis of a real-time polymerase chain reaction and a DNA chip and a method for integrated analysis using the same.

BACKGROUND

Currently, methods for analyzing a target gene of an analyte, that are widely conducted in a molecular diagnosis field, may be largely classified into two, a relative or absolute quantitative method of measuring expression degree of the target gene and the copy number thereof and a qualitative method of analyzing presence or absence of the target gene and the genotype thereof.

Among the methods for analyzing a target gene of an analyte, the real-time polymerase chain reaction (PCR) is a representative quantitative method, which is employed in measuring the expression degree of the target gene and the copy number thereof.

The real-time PCR method employs an apparatus where a PCR apparatus (thermal cycler) and a spectrophotometer are integrated with each other, and analyzes the amount of DNA or RNA fed or present at the early time by monitoring a procedure of producing amplification products of the target gene in real time during an amplification procedure, without a separate electrophoresis procedure for confirming PCR products after the PCR procedure. More specifically, the real-time polymerase chain reaction (PCR), where a fluorescent material is applied to the PCR method, may real-time detect and quantitatively analyze the degree of emission of the fluorescent material increasing in proportion to amplification of a target gene existing in the specimen during the reaction, thereby promptly and accurately analyzing the expression type of the target gene and the copy number thereof. As for the method of obtaining the fluorescent signal in the real-time polymerase chain reaction, there are largely a non-specific detection method and a specific detection method. As for the non-specific detection method, a fluorescent body (e.g., SYBR Green I, BEBO, BOXTO, EvaGreen, etc.) emitting a fluorescent material signal when being intercalated in the DNA double strands is used, and the entire fluorescent signal of double strands formed during the gene amplification is measured. As for the specific detection method, a fluorescent body is intercalated in a short oligonucleotide strand having a specific sequence that is complementarily bindable to a target gene to thereby form a probe (e.g., TaqMan probe, Molecular Beacon, Light-Up probe, Hybridization probe, or the like), and when the short oligonucleotide probe is amplified together with the target gene, a fluorescent signal generated from the short oligonucleotide probe in proportion to gene amplification is measured.

In the real-time polymerase chain reaction using the TaqMan probe in the specific detection method, a principle thereof is the same as that of a general PCR in view of using two primers, but an oligonucleotide probe chemically bound to a fluorescent material needs to be used. As for the TaqMan probe, FAM or the like as a reporter fluorescent material is attached to a 5' end thereof and TAMRA or the like as a quencher material of offsetting a fluorescence of the reporter fluorescent material is attached to a 3' end thereof. When the TaqMan probe is added to the PCR reactive solution, the TaqMan probe is annealed to the template DNA due to annealing with the template DNA during the PCR procedure, but the fluorescence is not detected by the offsetting action of the reporter and the quencher material. When the TaqMan probe hybridized with the template DNA is disintegrated due to activation of 5'. 3' exonuclease of the Taq DNA polymerase at the time of extension by the Taq DNA polymerase during the PCR procedure, FAM or the like, which is a fluorescent material, is isolated to thereby cancel the offset by the quencher material, resulting in emitting a fluorescence. Hence, the amount of amplified products generated may be measured by analyzing the amount of fluorescence detected.

Meanwhile, in the real-time polymerase chain reaction (PCR) using SYBR Green I in the non-specific detection method, the entire fluorescence is monitored. This method employs a principle where a fluorescent material is intercalated in the double strand DNA chain. SYBR Green I, which is a fluorescent material, is added at the time of PPCR reaction, to thereby detect the amount of fluorescence emitting in proportion to amplification of PCR products, and thus, the generation amount of amplified products may be measured and the melting point of the amplified DNA may be measured.

In addition, as for qualitative method used in analyzing the presence or absence of a target gene and the genotype thereof among the methods of analyzing a target gene, there is recently a DNA microarray (DNA chip) method capable of simultaneously detecting several tens to several tens of hundreds of kinds of genes on one sheet of slide through the combination of molecular biological technology and electronic engineering technology.

More specifically, as a method of using a microarray-fixed chip where oligonucleotide, PAN, or cDNA, capable of detecting a target gene is used as a probe, there is a microarray chip. According to this method, the amplified products after the PCR reaction is hybridized with a target microarray chip, to thereby be bound to several kinds of probes (oligonucleotide, PAN, or cDNA) immobilized on a surface of the chip solid (glass, plastic, membrane, silicon, etc.), and then the presence or absence of the binding may be determined by a fluorescent material signal labeled on the amplified product, and thus, this method is useful in analyzing various types of genotypes. However, the test procedure is complicated and a somewhat large amount of time is required, and the results are not visually confirmable by the naked eyes to thereby require a separate fluorescent analysis apparatus.

Recently, in the case of diseases by infectious bodies in a molecular diagnosis field as above, as various concepts of diagnosis and therapy are applied, the method of analyzing a target gene of an analyte simultaneously and complexly requires quantitative information of the copy number for confirming the infectious degree through a real-time polymerase chain reaction and qualitative information of the genotype by utilizing a microarray chip for prescription of an appropriate therapeutical agent by confirming the kind of infectious body. According to this purpose, the real-time polymerase chain reaction and the microarray chip analysis method are independently used in combination with each other.

However, according to the combination of the analysis methods above, experiments for the analysis methods are sequentially carried out in different reactors, and analyzed, and thus, a large amount of labor and time are still required and inconvenience remains. In addition, it is difficult to automate the analysis methods in a single device. Even though an apparatus for automating the simple combination of the analysis methods is manufactured, a large space for the installing the apparatus is required and the apparatus is very expensive, and thus, it is not easy to routinely use the apparatus for molecular diagnosis in a hospital. Therefore, development of a technology for solving these problems is really needed.

RELATED ART DOCUMENT

Patent Document (Patent Document 1) KR 10-1068939 B1, (Sep. 23, 2011)

SUMMARY

Therefore, with respect to a method of analyzing a target gene of an analyte, the present inventors found a method for integrated analysis of a biomaterial, capable of being conveniently used by anyone, and accurately and efficiently detecting a target gene, by performing a quantitative method and a qualitative method in a single reactor in a one-stop manner, and completed the present invention.

An embodiment of the present invention is directed to providing a method for integrated analysis of a biomaterial, capable of simultaneously performing quantitative analysis or qualitative analysis using a polymerase chain reaction or a real-time polymerase chain reaction and qualitative analysis using a DNA chip, on a plurality of genes.

More particularly, an embodiment of the present invention is directed to providing an apparatus for integrated analysis of a biomaterial and a method for integrated analysis using the same, capable of simultaneously and integratedly performing quantitative analysis or qualitative analysis using a polymerase chain reaction or a real-time polymerase chain reaction and qualitative analysis using a DNA chip in a single reactor.

In order to achieve the objects above, the present invention provides a method for integrated analysis of a biomaterial and an apparatus for integrated analysis using the same, capable of simultaneously performing quantitative analysis or qualitative analysis using a polymerase chain reaction or a real-time polymerase chain reaction and qualitative analysis using a DNA chip.

The method for integrated analysis of a biomaterial according to the present invention is characterized by simultaneously performing quantitative analysis or qualitative analysis using a polymerase chain reaction or a real-time polymerase chain reaction and qualitative analysis using a DNA chip in a single reactor.

For the integrated analysis, a single reactor where a biochip is formed on a bottom surface or a lateral surface inside the reactor, or on a rod extended from a lower side of a reactor coupler may be used.

In the present invention, the reactor includes both a reactor container and a cap coupled with an upper portion of the reactor container, and the cap may include the reactor coupler of the present invention.

Hereinafter, the present invention will be described in detail.

The present invention provides a method for integrated analysis of a biomaterial, characterized by simultaneously performing quantitative analysis or qualitative analysis of a reaction product amplified by using a polymerase chain reaction or a real-time polymerase chain reaction and qualitative analysis of the reaction product by a biochip having a target gene probe immobilized thereon in a single reactor, wherein in the single reactor, the biochip is formed on a bottom surface or a lateral surface inside the single reactor, or on a rod extended from a lower side of a reactor coupler of the single reactor. FIGS. 1 and 2 are provided for reference.

In the present invention, the target gene probe may include at least one material selected from peptide, protein, nucleic acid, peptide nucleic acid (PNA), aptamer, and antibody.

The probe according to the present invention may be obtained by labeling at least one site of any nucleotide sequence of the target gene with DNA intercalating fluorescent, phosphorescent, or radioactive material.

The fluorescent material of the probe may be at least one selected from the group consisting of Pyrene, Cyanine 2, GFP, Calcein, FITC, Alexa 488, FAM, Fluorescein Chlorotriazinyl, Fluorescein, Rhodamine 110, Oregon Green, Magnesium Green, Calcium Green, JOE, Cyanine 3, Tetramethylrhodamine, TRITC, TAMRA, Rhodamine Phalloidin, Pyronin Y, Lissamine, ROX, Calcium Crimson, Texas Red, Nile Red, Cyanine 5, and Thiadicarbocyanine.

In the present invention, as the single reactor, at least one selected from a plate having a plurality of wells, a test tube, a tube, and a biomaterial detecting device including a rod extended from a lower side of a reactor coupler may be used. Any reactor that can perform PCR may be used without limitation.

In the present invention, the single reactor is characterized to be a plate having a plurality of wells, or a biomaterial detecting device including a rod extended from a lower side of a reactor coupler.

The plate having a plurality of wells according to the present invention is characterized by having a well structure with two or more steps, and the plate having a plurality of wells may be divided so as to have a desired number of wells.

In the present invention, the plate having a plurality of wells includes a plurality of wells concavely formed in one surface of a plate. The well includes an upper well 210 and a lower well 220 below the upper well 210, the lower well 220 having a smaller diameter than the upper well 210. A biochip is formed on a bottom of the lower well 220. FIG. 3 is provided for reference.

More specifically, as shown in FIG. 3, upper wells 210 and lower wells 220 may be formed in various diameters and depths in a plate 1000 having a plurality of wells. In the present invention, the well is formed in a micro unit, such that a sample for a biomaterial reaction and an oil for protecting the sample above the sample are contained therein.

The plate 1000 having a plurality of wells may be manufactured by the method below.

That is, as for the method of forming the upper well 210 and the lower well 220, first, a mask pattern of resist or the like is formed on an upper surface of the plate 100, such that a portion thereof corresponding to the diameter of the upper well 210 is emptied, and then etching is performed, to thereby form the upper well 210 having a particular depth. In addition, after the upper well 210 is formed, a doughnut type of mask pattern is again formed on a bottom surface of the upper well 210 such that a portion thereof corresponding to the diameter of the lower well 220 is emptied, and then etching is again performed, to thereby form the lower well 220 having a particular depth. In addition, the above mask patterns may be removed and washed, to thereby form a well structure having a desired shape (having two steps).

As another method, the well 200 may be formed through physical processing, and the well 200 may be formed to have two steps as described above, by using various methods, such as, cut processing, laser processing, discharge processing, or the like, depending on the material of the plate 100.

The plate 1000 having a plurality of wells of the present invention constituted as above is used in a gene amplification reaction and the like, and for the use thereof, as shown in (B) of FIG. 3, a sample 400 to be tested is injected into the lower well 220 and an oil 500 for protecting the sample 400 is injected into the upper well 210 above the lower well 220. Hence, the oil 500 injected in the upper well 210 is covering the sample 400 contained in the lower well 220. Here, in the case where the well is formed to have one step, the sample is injected thereinto by a predetermined height and the oil is injected thereon, so that an upper surface of the sample is covered with the oil layer. However, the oil and the sample may lean toward one side, or may be mixed with each other. Even though they are not mixed with each other at the time of injection, the heating for the reaction of the sample may cause the oil and the sample to lean toward one side or mixed with each other, thereby deteriorating reliability of the biomaterial reaction.

Therefore, in the plate 1000 having a plurality of wells according to the present invention, the well is formed to have two steps, so that the oil covers the sample, but the sample and the oil is not mixed with each other due to the physical structure thereof, and thus, evaporation of the sample due to heating of the sample can be prevented. Also, since the well is formed to have two steps, the injection amount of sample and the injection amount of oil can be uniformly controlled. In addition, the sample is covered with the oil, to thereby prevent external impurities from infiltrating to the sample, and thus, reliability in analysis can be improved.

In the present invention, the biomaterial detecting device includes a reactor and a rod extended from a lower side of a reactor coupler. A biochip is formed on a lower side of the rod, and the rod is detachable from the reactor coupler. FIG. 4 is provided for reference.

More specifically, as shown in FIG. 4, in the biomaterial detecting device 2000, a head 2100 may be formed in a flat plate type, a block shape, or the like. When the biomaterial detecting device is manually transferred by a hand of the user or coupled with or decoupled from the reaction container 2700 containing the sample, the head may receive a force applied thereto or may be combined with an automated device to be movable.

The reactor coupler 2200 is protruded downwardly from the head 2100, and the reactor 2700 may be outwardly inserted into and coupled with the reactor coupler 2200. Here, a groove is formed in an outer circumferential surface of the reactor coupler 2200 along a circumferential direction thereof, and an elastic sealing member such as O-ring is combined with the groove, so that an inside of the tube can be sealed when the reactor is inserted into the reactor coupler 2200.

The rod 2300 may be extended downwardly from the reactor coupler 2200, and may be lengthily formed in a stick shape along a lower direction thereof. Here, the rod 2300 preferably has a smaller diameter than the reactor coupler 2200. Since the rod 300 is contacted with the sample such as a biomaterial solution, the rod 300 is preferably formed of glass having no reactivity with the sample.

In addition, the rod 2300 may be detachable from the reactor coupler 2200. That is, a hole is formed in a lower portion of the reactor coupler 2200, and the rod 2300 is inserted into the hole and coupled with the reactor coupler 2200. Thus, the rod 2300 may be replaced, as necessary.

In addition, the biochip 2400 is formed on the lower side of the rod 2300. The biochip 2400 is immersed in the sample to thereby react with the sample, and thus, can detect a target material.

The biomaterial detecting device 2000 may include a head 2100, a reactor coupler 2200, a rod 2300, and a biochip 2400. As shown in B of FIG. 4, the reactor coupler 2200 may be inserted into and coupled with the reactor 2700 containing the sample. Here, the biochip 2400 formed at the lower side of the rod 300 is immersed in the sample 2800 in the reactor 2700. Hence, gene application and hybridization may be allowed to proceed in the reactor 2700, and simultaneously, the amplified gene may react with the target gene probes of the biochip 2400 during the hybridization procedure, to thereby induce combination and reaction with the target gene probes.

That is, the real-time polymerase chain reaction (PCR, gene amplification) was carried out in the reactor 2700; a fluorescent signal generated in the reactor 2700 was real-time obtained by using a monitoring equipment; after that, hybridization with the probes immobilized on the biochip was carried out; the rod 2300 and the biochip 2400 were separated from the reactor 2700 and then washed; a fluorescent signal reacting with the probe was obtained by using an exclusive fluorescent detector; and biochip analysis was carried out. Therefore, the real-time PCR and the biochip analysis can be integratedly carried out in a single reactor.

The method for integrated analysis of a biomaterial according to the present invention is characterized by detecting target nucleic acid of *Mycobacterium tuberculosis* or hepatitis B virus, and more particularly performing diagnosis of the presence or absence of *Mycobacterium tuberculosis*, diagnosis of the presence or absence of *Mycobacterium tuberculosis* having antibiotic resistance or diagnosis of the presence or absence of hepatitis B virus (HBV), and detection of drug-resistance modified hepatitis B virus (HBV).

More particularly, the target gene primer and probe for differentiating *Mycobacterium tuberculosis* from *Nontuberculous mycobacteria* may include an oligonucleotide containing a nucleotide sequence capable of specifically binding to a target gene of only *Mycobacterium tuberculosis* or a complementary nucleotide sequence thereof, and more preferably, may include at least one primer and probe including a nucleotide sequence of SEQ. ID NOs: 1 to 3 or a complementary nucleotide sequences thereof.

In addition, the target gene primer and probe for detecting antibiotic resistance may include a nucleotide sequence capable of specifically binding to a target gene inducing antibiotic resistance, for example, a nucleotide sequence capable of specifically reacting with a nucleotide sequence inducing resistance to Rifampin (RMP) and Isoniazid (INH), that is, any oligonucleotide having a complementary nucleotide sequence, but preferably include an oligonucleotide including a point mutant nucleotide sequence of the rpoB gene inducing Rifampin resistance or a complementary nucleotide sequence thereof, and an oligonucleotide including a point mutant nucleotide sequence of the katG gene and the inhA gene inducing Isoniazid resistance, and more preferably include at least one primer and probe including a nucleotide sequence of SEQ. ID. NOs: 4 to 35 or a complementary nucleotide sequence thereof.

The target gene primer and probe for detecting drug-resistant HBV may include an oligonucleotide having a nucleotide sequence capable of specifically binding to the target gene inducing Lamivudine resistance, and preferably an oligonucleotide including a point mutant nucleotide sequence having mutations at Codons 528, 529, and 514 of Region B and Codons 552, 548, and 555 of Region C of the HBV DNA polymerase gene inducing lamivudine resistance, and more preferably at least one primer and probe including a nucleotide sequence of SEQ ID. NOs: 36 to 46 or a complementary nucleotide sequence thereof.

In order to simultaneously detect the resistance to a newly developed antibiotic or drug in addition to the target gene set forth above, the present invention may further include an oligonucleotide including a nucleotide sequence related to a newly identified antibiotic or a mutant nucleotide sequence related to drug resistance.

In the probe according to the present invention, the fluorescent material of the probe for quantitatively analyzing the reaction product amplified by using a real-time polymerase chain reaction (PCR) and the fluorescent material of the probe for qualitatively analyzing the amplified reaction product after hybridization may have different wavelengths.

More specifically, the probe according to the present invention employed the FAM fluorescent material for quantitative analysis of the reaction product amplified by using a real-time polymerase chain reaction (PCR) and employed the Cy3 fluorescent material for qualitative analysis after hybridization with the amplified reaction product.

For specific example, the integrated analysis may be performed by using the plate 1000 having a plurality of wells or the biomaterial detecting device 2000 according to the present invention.

As shown in FIG. 1, a plurality of target gene probes are arrayed on a surface of □ and □, and a real-time PCR reagent and a target gene primer were put into a reactor containing the target gene probe, as indicated by □, then gene amplification is carried out. While the reaction as shown in □ occurs during the gene amplification, a fluorescent material (e.g., FAM) signal generated in the reactor as indicate by □ is acquired by a camera in real-time, and thus, the quantitatively analyzed value is obtained. The reaction product after gene amplification is subjected to a DNA microarray reaction as shown in □ through only the temperature change without separate treatment. The qualitative analysis of the resultant material may be carried out, by, after washing, reading a fluorescent material (e.g., Cy3) signal, which is different from the fluorescent signal detected in the real-time PCR, by using a fluorescent detector, and thereby obtaining a genotype signal as shown in ⑧.

DETAILED DESCRIPTION OF MAIN ELEMENTS

Figure 1:
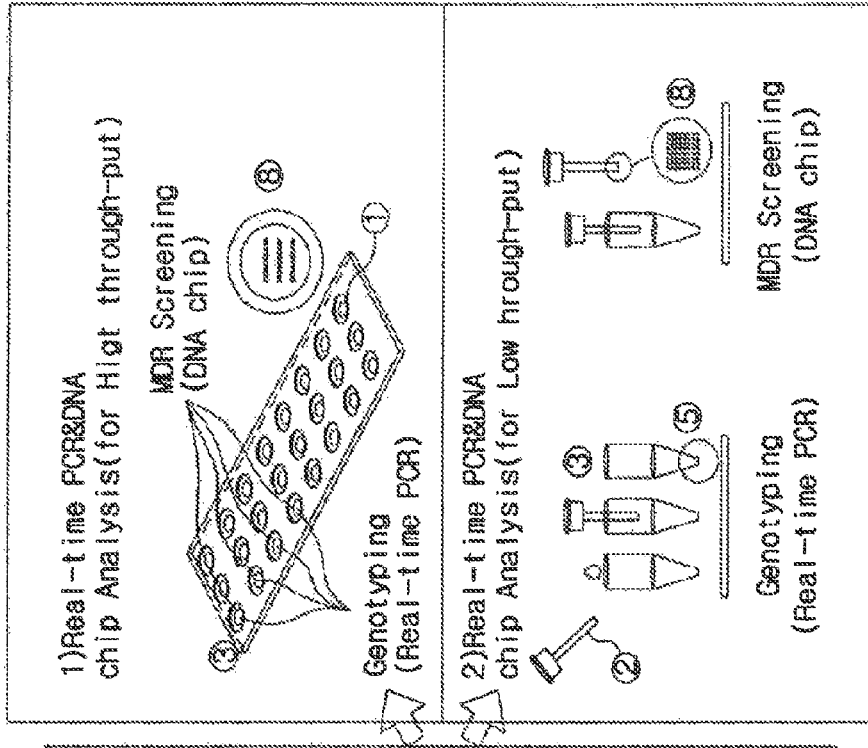
FIG. 1 is a schematic view of a method for integrated analysis of a biomaterial according to the present invention.
Figure 2:
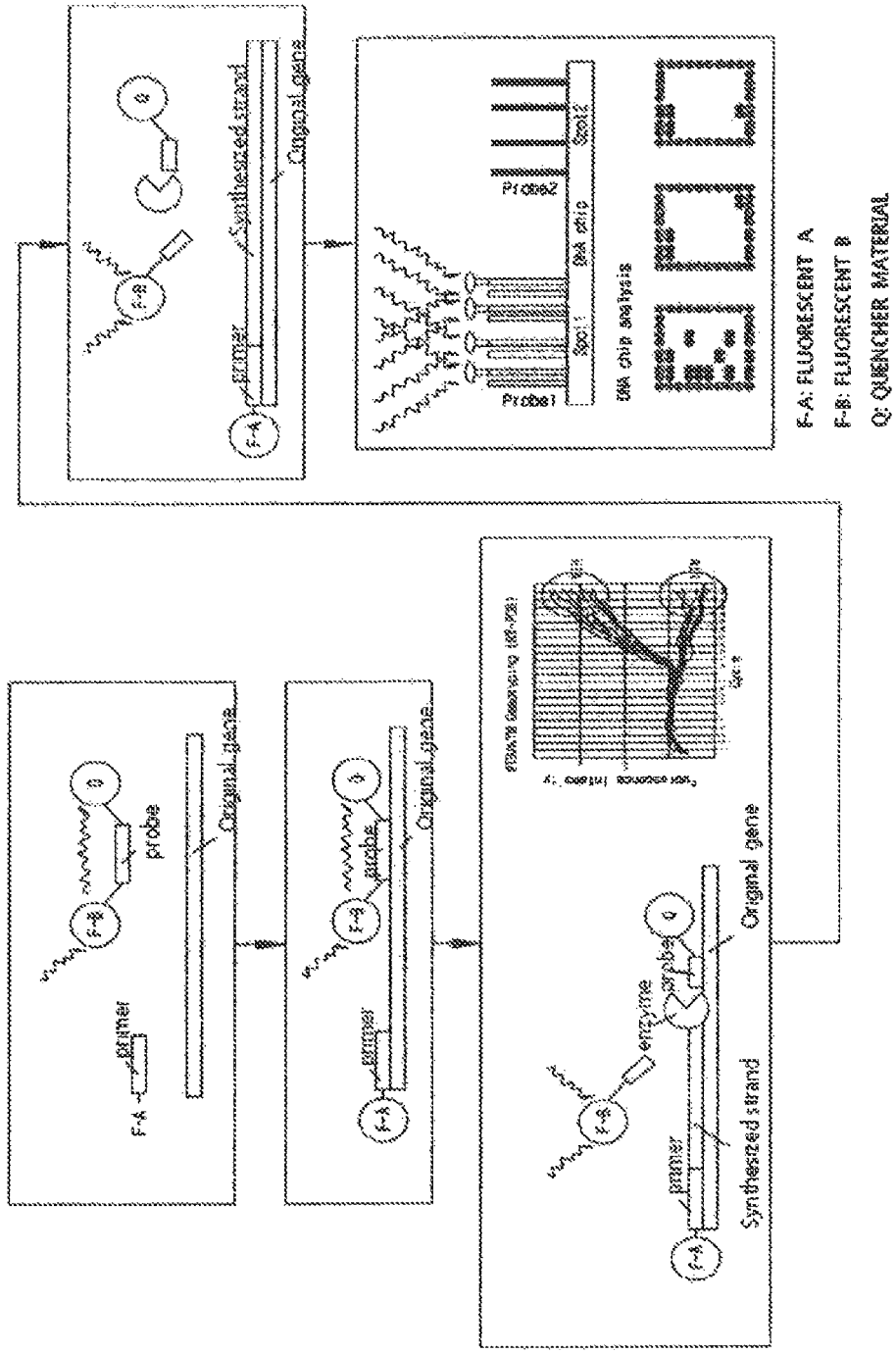
FIG. 2 shows an operating principle of the method for integrated analysis of a biomaterial according to the present invention.
Figure 3:
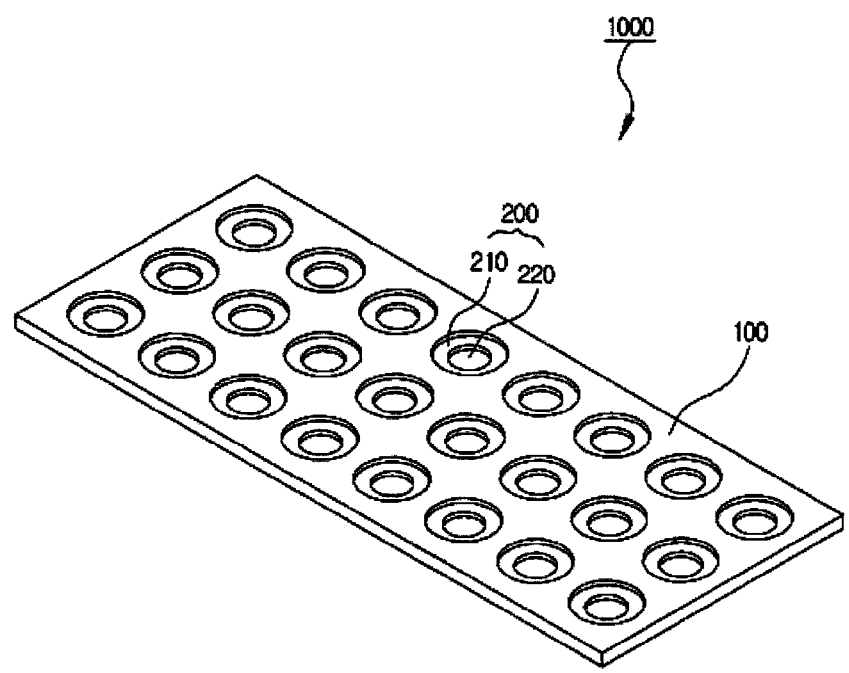
FIG. 3 shows a perspective view (A) of a plate having a plurality of wells according to the present invention, and a cross-sectional view (B) of a structure where a sample and an oil are contained in each of the wells of the plate having a plurality of wells.
Figure 3:
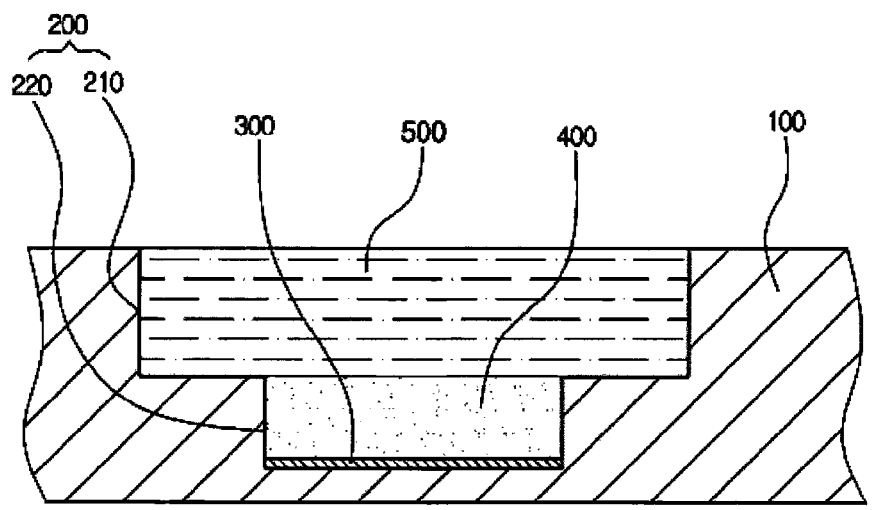
Figure 4:
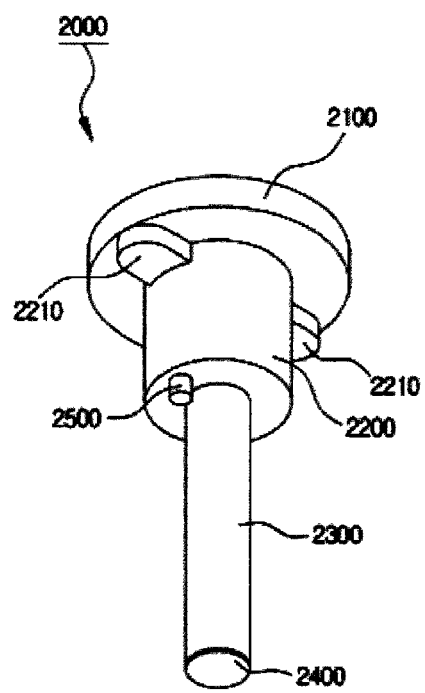
FIG. 4 shows a perspective view (A) of a biomaterial detecting device according to the present invention, and a cross-sectional view (B) of a structure where the biomaterial detecting device is coupled with a reactor containing a sample.
Figure 4:
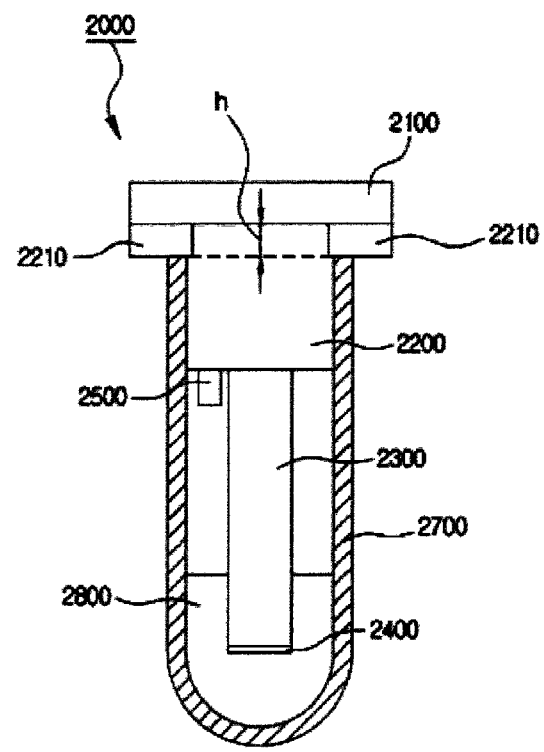
Figure 5:
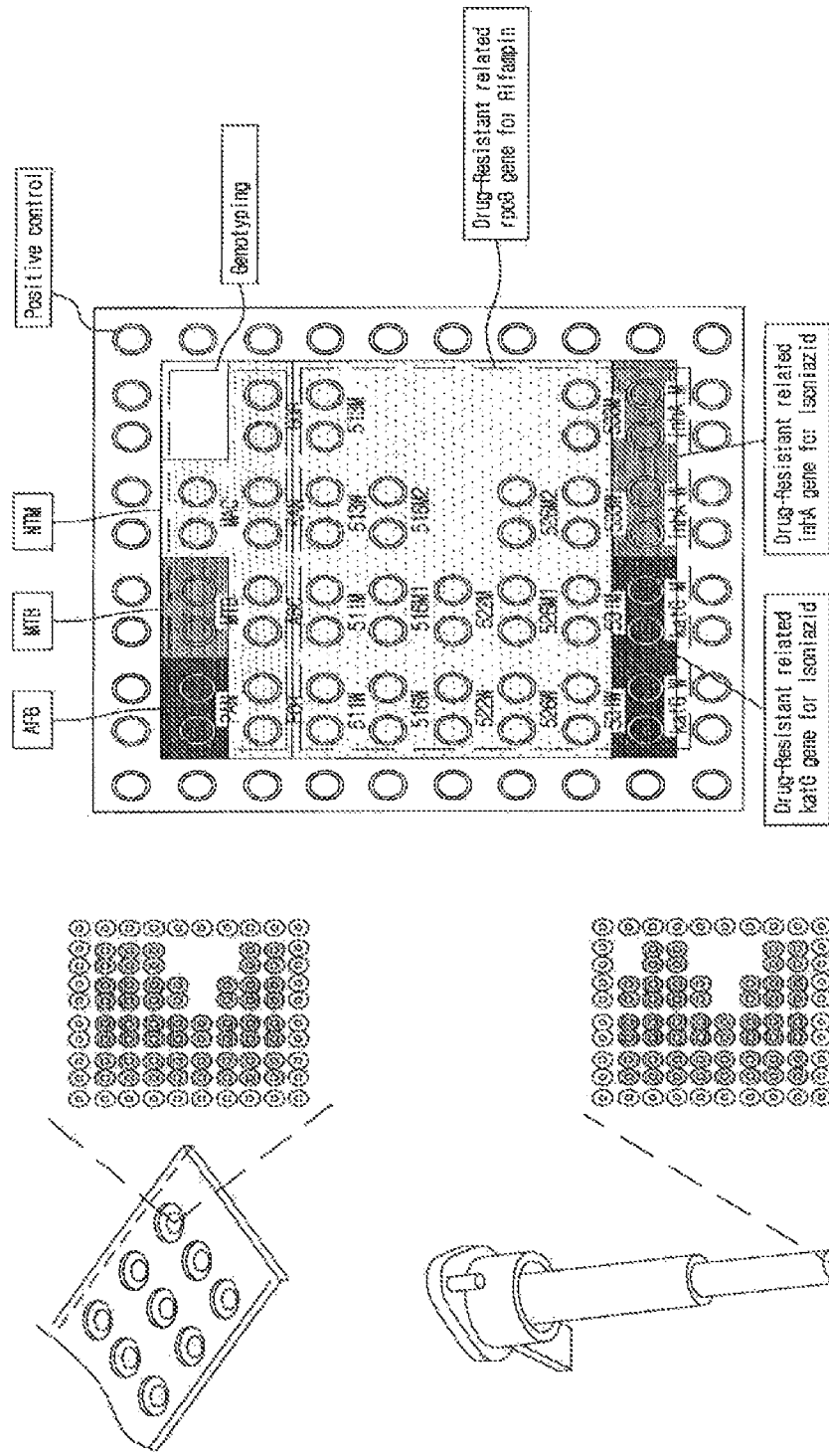
FIG. 5 shows a result of detecting antibiotic resistance of *Mycobacterium tuberculosis* according to Example 4 of the present invention.
Figure 6:
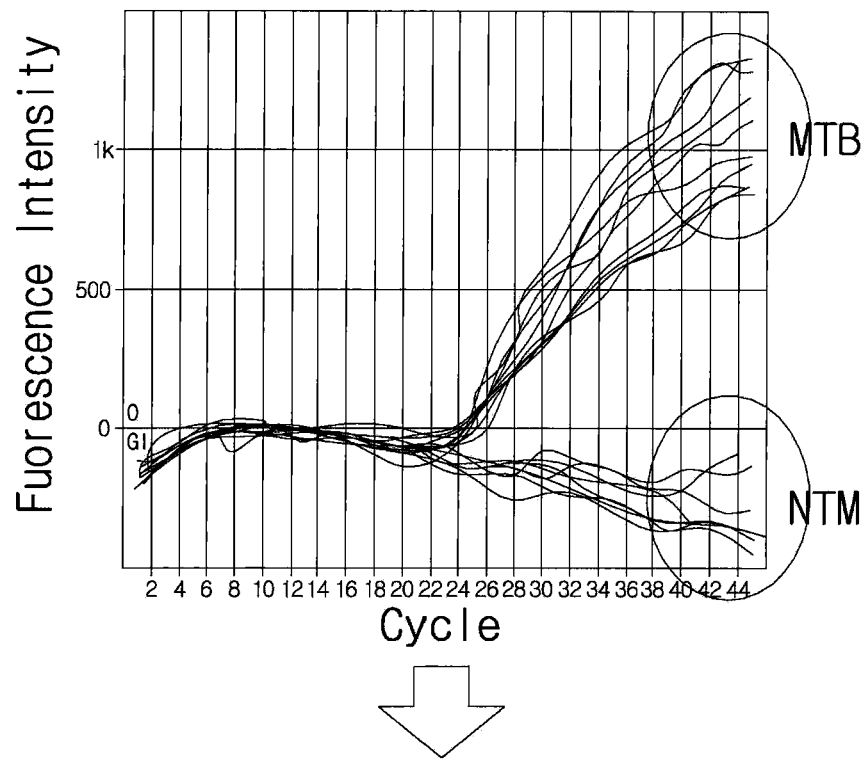
FIG. 6 shows differentiation of *Mycobacterium tuberculosis* according to the present invention from *Nontuberculous mycobacteria*, and a result of detecting multidrug resistance of *Mycobacterium tuberculosis*.
Figure 6:
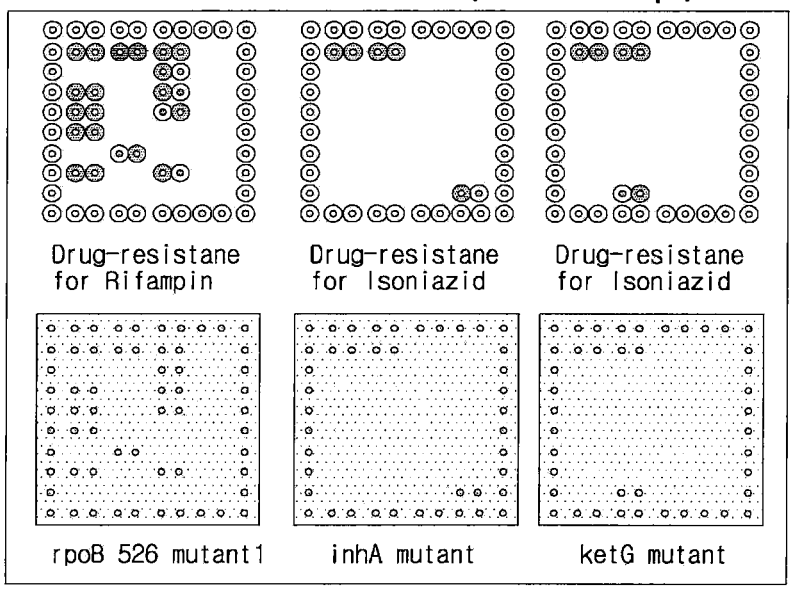

1000: plate having a plurality of wells (of the present invention)
100: plate
200: well
210: upper well
220: lower well
300: biochip
400: specimen
500: oil
2000: biomaterial detecting device (of the present invention)
2100: head
2200: reactor coupler 2210: protrusion
2300: rod
2400: biochip
2500: direction indicator
2600: adaptor
2700: reactor
2800: sample

DETAILED DESCRIPTION OF EMBODIMENTS

The present invention will be described in more detail with reference to the examples below. However, the examples below are provided only for assisting in the understanding of the present invention, but the scope of the present invention is not limited to these examples.

Here, unless indicated otherwise, the terms used in the specification including technical and scientific terms have the same meaning as those that are usually understood by those who skilled in the art to which the present invention pertains, and detailed description of the known functions and constitutions that may obscure the gist of the present invention will be omitted.

Example 1

Manufacture of Primer and Probe (1) Manufacture of Primer for Differentiating *Mycobacterium tuberculosis/Nontuberculous mycobacteria* From Each Other and Probe for Real-Time PCR, and Primer and Probe for DNA Chip for Diagnosing Antibiotic Resistance An oligonucleotide primer, a probe for real-time PCR, and a probe for DNA chip, for differentiating *Mycobacterium tuberculosis* and diagnosing resistance to Rifampin (rpoB) and Ioniazid (inhA, katG) drugs, are shown in Table 1

(primers for differentiating *Mycobacterium tuberculosis*), Table 2 (probe for real-time PCR for differentiating *Mycobacterium tuberculosis*), Table 3 (primers for diagnosing antibiotic resistance), and Table 4 (probes for immobilizing a DNA chip for diagnosing antibiotic resistance).

The probes shown in Tables 1 and 2 were for quantitative analysis of a reaction product of the *Mycobacterium tuberculosis* amplified by using real-time PCR, and FAM was used as a fluorescent material and TAMRA was used as a quenching material. In order to perform hybridization of the amplified reaction product and then confirm qualitative analysis of genotype for diagnosing antibiotic resistance by the DNA chip, the Cy3 fluorescent material was attached to a primer for diagnosing antibiotic resistance in Table 3 below. Therefore, during the gene amplification procedure, the probe for diagnosing antibiotic resistance having the Cy3 fluorescent attached thereto and previously immobilized on a surface of the DNA chip reacted with the amplified reaction product, to thereby generate a signal.

TABLE 1

Primers for Detecting *Mycobacterium tuberculosis*/Nontuberculous mycobacteria

| SEQ. ID NO. | Identified Bacillus (Target Gene) | Primer Name | Nucleotide Sequence |
|---|---|---|---|
| 1 | Mycobacteria | ITSF-2 | 5'-GCTTTCTAAGGAGCACCACG-3' |
| 2 | | Mycom2R | 5'-Cy3-TGGATAGTGGTTGCGAGCAT-3' |

TABLE 2

Probe for Real-Time PCR for Detecting *Mycobacterium tuberculosis*/Nontuberculous mycobacteria

| SEQ. ID NO. | Identified Bacillus (Target Gene) | Probe Name | Nucleotide Sequence |
|---|---|---|---|
| 3 | TB complex | MTB-02 | 5'-FAM-TGGTGGGGCGTAGGCCGTGA-TAMRA-3' |

TABLE 3

Primer for Diagnosing Antibiotic Resistance

| SEQ. ID NO. | Identified Bacillus (Target Gene) | Primer Name | Nucleotide Sequence |
|---|---|---|---|
| 4 | Rifampin(rpoB) | rpoB F | 5'-GCTGGTCATGTTCGCGATCG-3' |
| 5 | Rifampin(rpoB) | rpoB R | 5'-Cy3-ACCGGTTACCGCCAGCGAG-3' |
| 6 | Isoniazid(inhA) | Inh F | 5'-ACCCCAGTGCGAAAGTTCCC-3' |
| 7 | Isoniazid(inhA) | Inh R | 5'-Cy3-GGTAACCAGG ACTGAACGGG-3' |
| 8 | Isoniazid(katG) | kat1 F | 5'-AAGAGCTCGTATGGCACCGG-3' |
| 9 | Isoniazid(katG) | kat4 R | 5'-Cy3-AGCGCCAGCAGGGCTCTTC-3' |

TABLE 4

Probe for immobilizing DNA Chip for Diagnosing Antibiotic Resistance

| SEQ. ID NO. | Identified Bacillus (Target Gene) | Probe Name | Nucleotide Sequence |
|---|---|---|---|
| 10 | Rifampin (rpoB) | 511W | 5'-CAGCCAGCTGAGCCAATTCA-3' |
| 11 | | 511M | 5'-AGCCAGCCGAGCCAA-3' |
| 12 | | 513W | 5'-CTGAGCCAATTCATG-3' |
| 13 | | 513M | 5'-CTGAGCCTATTCATGG-3' |
| 14 | | 516W | 5'-TTCATGGACCAGAACA-3' |
| 15 | | 516M1 | 5'-TTCATGGTCCAGAACA-3' |
| 16 | | 516M2 | 5'-ATTCATGTACCAGAACA-3' |
| 17 | | 516M3 | 5'-ATTCATGTTCCAGAACA-3 |
| 18 | | 522W | 5'-CTGTCGGGGTTGAC-3' |
| 19 | | 522M | 5'-CTGTTGGGGTTGAC-3' |
| 20 | | 526W | 5'-GTTGACCCACAAGCGCCGA-3' |
| 21 | | 526M1 | 5'-GGTTGACCTACAAGCGC-3' |
| 22 | | 526M2 | 5'-GGTTGACCGACAAGCGC-3' |
| 23 | | 526M3 | 5'-TTGACCCGCAAGCGC-3' |
| 24 | | 526M4 | 5'-TTGACCCTCAAGCGC-3' |
| 25 | | 526M5 | 5'-TTGACCCCCAAGCGC-3' |
| 26 | | 531W | 5'-CGACTGTCGGCGCTG-3' |
| 27 | | 531M1 | 5'-CGACTGTTGGCGCTG-3' |
| 28 | | 531M2 | 5'-CCGACTGTGAGCGCT-3' |
| 29 | | 533W | 5'-GGCGCTGGGGCCCGGC-3' |
| 30 | | 533M | 5'-GTCGGCGCCGGGGCCCG-3' |
| 31 | Isoniazid (inhA) | 315W | 5'-ATCACCAGCGGCATC-3' |
| 32 | | 315M1 | 5'-ATCACCACCGGCATC-3' |
| 33 | | 315M2 | 5'-ATCACCAACGGCATC-3' |
| 34 | | inhW | 5'-GGCGAGACGATAGGT-3' |
| 35 | | inhM | 5'-GGCGAGATGATAGGT-3' |

(2) Manufacture of Primer and Probe for Detecting Drug-Resistant Hepatitis B Virus Primers and target probes for detecting drug-resistant HBV were manufactured to include point mutant nucleotide sequences at Codon 552, 548, and 555 of the YMDD motif of Region C and Codon 528, 529, and 514 of Region B in the HBV DNA polymerase gene inducing Lamibudine resistance, and are shown in Tables 5, 6, and 7 below.

The probes were manufactured by using FAM as a fluorescent material for quantitative analysis of the reaction product amplified by using the real-time polymerase reaction (PCR), and selecting the Cy3 fluorescent material for qualitative analysis after hybridization with the amplified reaction product.

Among the probes below, the primers for detecting the Hepatitis B virus (Table 5) and the probe for real-time PCR for detecting the Hepatitis B virus (Table 6) are for quantitative analysis of the reaction product of the Hepatitis B virus amplified by using the real-time polymerase chain reaction (PCR). Here, FAM was used as a fluorescent material and TAMRA was used as a quencher material. In order to perform hybridization of the amplified reaction product and then confirm qualitative analysis of the genotype for diagnosing antibiotic resistance on the DNA chip, the Cy3 fluorescent material was attached to a primer for diagnosing antibiotic resistance in Table 5 below. Therefore, during the gene amplification procedure, the probe for diagnosing antibiotic resistance of Table 7, having the Cy3 fluorescent attached thereto and previously immobilized on a surface of the DNA chip, reacted with the amplified reaction product, to thereby generate a signal.

TABLE 5

Primers for Detecting Hepatitis B Virus

| SEQ ID. NO. | Primer Name | Nucleotide Sequence |
|---|---|---|
| 36 | BF105 | 5'-TCCTGCTGCTATGCCTCATC-3' |
| 37 | BR112 | 5'-Cy3-TCCCTTAACTTCATGGGATATGTCGACGGAA-3' |

TABLE 6

Probe for Real-Time PCR for Detecting Hepatitis B Virus

| SEQ ID. NO. | Probe Name | Nucleotide Sequence |
|---|---|---|
| 38 | HB-P | 5'-FAM-TGGTATTGGGGCCAAGTCT-TAMRA-3' |

TABLE 7

Probes for immobilizing DNA Chip for Diagnosing Antibiotic Resistance

| SEQ ID. NO. | For Detecting Lamibudine | Probe Name | Nucleotide Sequence |
|---|---|---|---|
| 39 | For Detecting Wild Type of Codon 514 | 514WF1 | TGGGCTTTCGCAAAA |
| 40 |  | 514WF2 | TGGGCTTCCGCAAAA |
| 41 | For Detecting Mutant of Codon 514 | 514ML1 | TGGGCTTACGCAAAA |
| 42 |  | 514ML2 | TGGGCTTGCGCAAAA |
| 43 |  | 514ML3 | TGGGCCTTCGCAAAA |
| 44 |  | 514ML4 | TGGGCCTCCGCAAAA |
| 45 |  | 514ML5 | TGGGCTTACGCAAAA |
| 46 |  | 514ML6 | TGGGCCTAGGCAAAA |

Example 2

Attachment of Probe to Supporter

Each of the probes for quantitative analysis and qualitative analysis, which were manufactured in Example 1, was diluted to 100 pmol, and then transferred into a 96-well micro-plate. A spotting solution was added thereto, and then mixed to have 50 pmol. The probes were attached to a supporter such as a slide glass, a membrane, or the like, by using a microarray (Cartesian Technologies, PLXSYS 7500 SQXL Microarrayer, USA).

In order to remove the probes that were unattached on a surface of the supporter, the thus obtained support was washed with a 0.2% sodium dodecyl sulfate (SDS) solution at room temperature. The thus obtained support was washed with a sodium borohydride solution, and then again washed with boiling distilled water. The thus obtained support was washed with a 0.2% SDS and distilled water at room temperature, and then the surface of the support was completely dried by using a centrifugal separator, to thereby complete the manufacture of a microarray (biochip).

Example 3

Manufacture of a Biomaterial Detecting Device

A biomaterial detecting device was manufactured by fixing the biochip manufactured in Example 2 on a bottom of a stick type rod.

Example 4

Separation of Genome DNA from Bacteria (1) Separation of Genome DNA from *Mycobacterium tuberculosis*

As for *Mycobacterium tuberculosis* used in the present experiment, bacteria were obtained from the Korean National Tuberculosis Association and specimens were obtained from the National Masan Tuberculosis Hospital. The InstaGene matrix (Bio-Rad Co., USA) was used in order to extract DNA thereof. 100 μl of InstaGene matrix was inputted in a 1.5 ml tube. The bacteria to be used in the present experiment were cultured in the solid medium (Ogawa medium), and then 1 platinum loop of bacteria cells were inputted and floated in the tube containing the InstaGene matrix. This was allowed to react in a constant-temperature water bath of 56° C. for 30 minutes, and then well mixed for 10 seconds, to thereby be homogenized. Then, this was subjected to heat-treatment at 100° C. for 8 minutes, and well stirred for 10 seconds. The mixture was centrifugally separated at 12,000 rpm for 3 minutes, and the separated supernatant was transferred to a new tube. This was used as a template DNA for real-time PCR reaction.

(2) Separation of Genome DNA from Hepatitis B Virus

The blood collected from a patient with hepatitis B virus was directly refrigerated to thereby be coagulated for 1 hour, and then the serum was centrifugally separated at 3000 rpm for 5 minutes. The obtained serum was stored at −70° C. The QIAamp DNA Blood Mini Kit (QIAGEN Inc., CA, USA) was used in order to extract DNA thereof. The kit was used to secure 200 μl of HBV DNA from the serum finally. This was used as a template DNA for real-time PCR reaction.

Example 5

Result Analysis (1) Detection of Presence or Absence of *Mycobacterium tuberculosis* and Antibiotic Resistance The biomaterial detecting device manufactured in Example 3 was installed in the tube containing a sample, and then the real-time PCR was carried out.

An FAM fluorescent signal generated in the tube during the gene amplification procedure was obtained in real time by using a camera; after that, hybridization was carried out; the cap was opened to separate the glass rod attached to the cap, which was then washed; a Cy3 fluorescent signal reacting with the probe was obtained by using an exclusive fluorescent detector; and then DNA chip analysis was carried out.

The results were tabulated in Table 6.

(2) Detection of Drug-Resistant Hepatitis B Virus

The biomaterial detecting device manufactured in Example 3 was installed in the tube containing a sample, and then the real-time PCR was carried out.

An FAM fluorescent signal generated in the tube during the gene amplification procedure was obtained in real time by using a camera; after that, hybridization was carried out; the cap was opened to separate the glass rod attached to the cap, which was then washed; a Cy3 fluorescent signal reacting with the probe was obtained by using an exclusive fluorescent detector; and then DNA chip analysis was carried out.

As confirmed from the results above, according to the method for integrated analysis of a biomaterial of the present invention, gene amplification was allowed to proceed and subsequently hybridization proceeds in a single reactor, thereby preventing contamination of the sample due to external factors, which may be caused while the sample was transferred for reaction, and automating a series of procedures such as injection of the sample, reaction of the biomaterial, and detection and analysis of results.

Further, the method for integrated analysis of a biomaterial according to the present invention can significantly shorten the time needed for detecting microorganisms harmful to humans, which are causes of various kinds of diseases as compared with the existing commercialized method, and be very economical in view of costs, and accurately and efficiently detect the target gene.

As set forth above, according to the method for integrated analysis of a biomaterial of the present invention, gene amplification proceeds and subsequently hybridization proceeds in a single reactor, thereby preventing contamination of the sample due to external factors, which may be caused while the sample is transferred for reaction, and automating a series of procedures such as injection of the sample, reaction of the biomaterial, and detection and analysis of results.

The method for integrated analysis of a biomaterial according to the present invention can significantly shorten the time needed for detecting microorganisms harmful to humans, which are causes of various kinds of diseases as compared with the existing commercialized method, and be very economical in view of costs, and accurately and efficiently detect the target gene.

---

What is claimed is:

1. A method for integrated analysis of a biomaterial in a sample using a biomaterial detecting device, characterized by simultaneously performing quantitative analysis of a reaction product amplified by using a real-time polymerase chain reaction (real-time PCR) and qualitative analysis of the reaction product by a biochip having a target gene probe immobilized thereon in a single reactor, said method comprises:
   (a) injecting a real-time PCR reagent, and a target gene primer into the single reactor, and performing gene amplification; and
   (b) conducting hybridization of the amplification reaction product with the target gene probe in the single reactor, only through the temperature change;
   wherein, the biomaterial detecting device comprises a reactor; a head; a reactor coupler protruded downwardly from the head; a first protrusion and a second protrusion formed on a first portion and a second portion of an outer circumferential surface of the reactor coupler, respectively, and also protruded from the bottom surface of the head; a rod extended downwardly from the reactor coupler; and the biochip formed on the lower side of the rod,
   the reactor coupler is to be coupled with a reactor in a manner a part of the reactor coupler is to be inserted into an inside of the reactor, and the rest of the reactor coupler is not to be inserted into the inside of the reactor,
   there is a space between the first protrusion and the second protrusion,
   the protrusions are formed so that the protrusion prevents the head from contacting the reactor, and the protrusions prevent all parts of the reactor coupler inserted into the inside of the reactor, and
   the rod is detachable from the reactor coupler to allow replacement of the rod.

2. The method of claim 1, wherein the target gene probe is selected from the group consisting of peptide, protein, nucleic acid, peptide nucleic acid, aptamer, and antibody.

3. The method of claim 1, wherein the biomaterial comprises a target nucleic acid of *Mycobacterium tuberculosis* or hepatitis B virus.

4. The method of claim 3, wherein the target nucleic acid of *Mycobacterium tuberculosis* or Hepatitis B virus is detected by using at least one target gene primer and at least one target gene probe selected from the group consisting of nucleotide sequences of SEQ ID NOs.: 1 to 46.

* * * * *